Sept. 14, 1976 J. PAVCIK Plant Pat. 3,951
ALMOND TREE
Filed Oct. 14, 1975
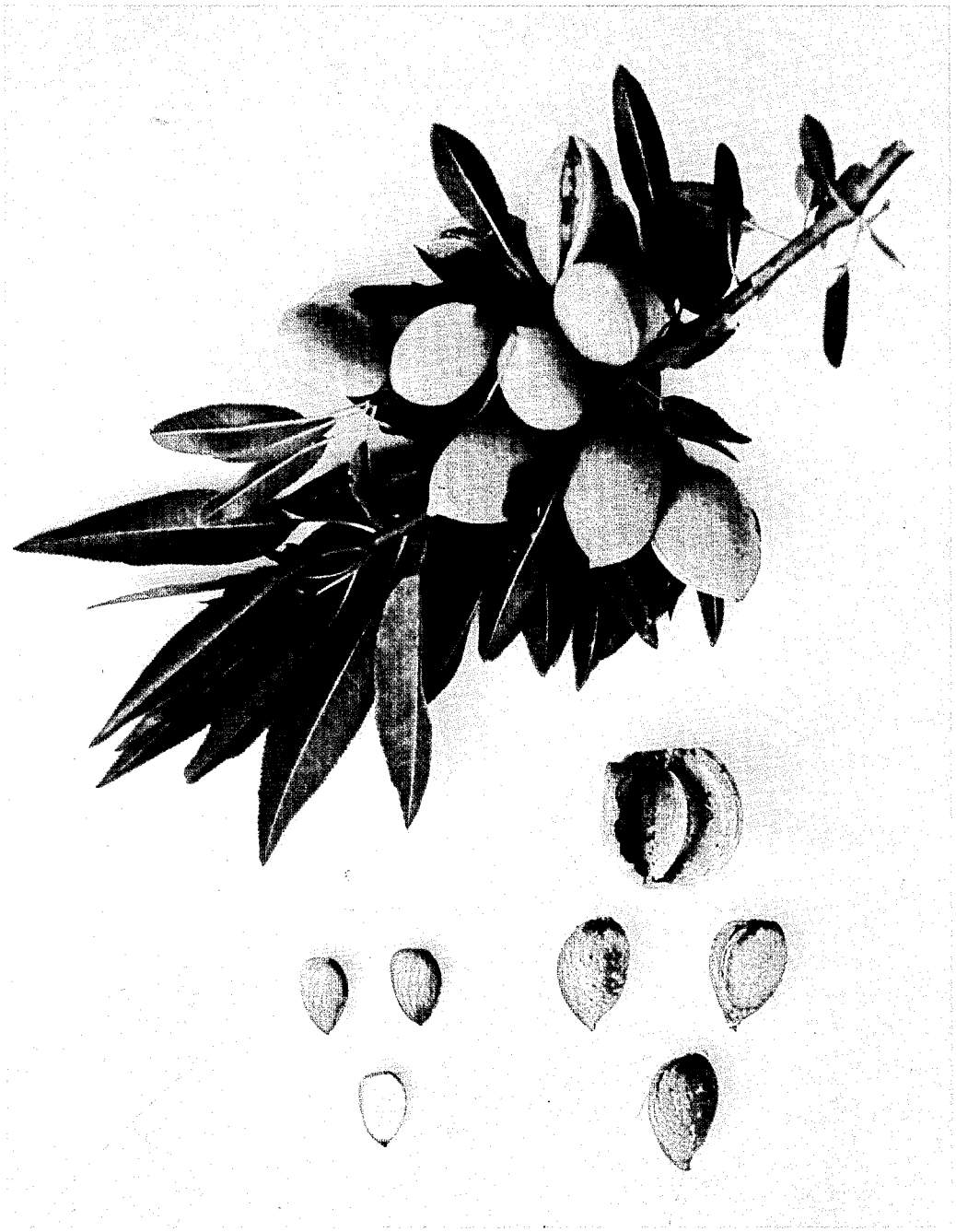

United States Patent

Plant Pat. 3,951

Patented Sept. 14, 1976

3,951

ALMOND TREE

Joseph Pavcik, 1187 Stanley Ave., Chico, Calif. 95926

Filed Oct. 14, 1975, Ser. No. 622,027

Int. Cl.[2] A01H *5/03*

U.S. Cl. Plt.—30 1 Claim

ABSTRACT OF THE DISCLOSURE

An almond tree generally characterized by vigor, large size, dense upright growth, stocky medium-textured trunk and branches, a spreading branching habit, abundant foliage with large, acutely pointed smooth-textured leaves of medium thickness, an early blooming period with white, very heavy bloom, and regular and very heavy bearing of early harvesting, medium size, soft shell nuts having medium size kernels.

ORIGIN OF THE VARIETY

The present variety of almond tree was discovered by me growing in an orchard of Nonpareil almond trees on my ranch located near Chico, Butte County, Calif.; the discovery having occurred by reason of my observation that the original tree of the present variety bore a much heavier crop than adjacent Nonpareil trees. I, therefore, continued to observe such original tree and ascertained that it was characterized by other distinctive features as will hereinafter appear.

ASEXUAL REPRODUCTION OF THE VARIETY

Subsequent to my discovery of the present variety of almond tree, the variety was successfully asexually reproduced as follows:

Budwood from the original tree of the variety was grafted onto peach rootstock; such reproduction having been undertaken, on my behalf, by a commercial nursery. The trees, as thus reproduced, were planted on my ranch located as aforesaid, and in maturity such trees ran true to the original tree in all respects.

SUMMARY OF THE VARIETY

The present variety of almond tree is generally characterized by vigor, large size, dense upright growth, stocky medium-textured trunk and branches, a spreading branching habit, abundant foliage with large, acutely pointed smooth-textured leaves of medium thickness, an early blooming period with white, very heavy bloom, and regular and very heavy bearing of early harvesting, medium size, soft shell nuts having medium size kernels.

The present variety of almond tree is more particularly characterized in the following respects:

The tree, in growth, is upright with a spreading branching habit generally like the Nonpareil, while the fruit wood is thick and similar to the Drake.

The blooming period is early, slow, long, and closer to the Nonpareil than any other commercial variety of almond tree, and hence is an excellent pollinator therefor.

The harvest period is early and substantially with the Nonpareil; the crop being much heavier, and the nuts being easy to harvest and hull.

The nuts have shells and kernels of generally the same shape and color as the Davey; the shells being soft and well-sealed.

All of the existing almond varieties, as mentioned herein, are unpatented.

BRIEF DESCRIPTION OF THE DRAWING

The drawing is an illustration, by photographic reproduction in color, of a twig with leaves and nuts; and, separately shown, a nut in open hull, nuts out of hull, and kernels out of shell.

DESCRIPTION OF THE VARIETY

The botanical details of this new and distinct variety of almond tree—with color definition (except those in common color terms) referenced to Maerz and Paul Dictionary of Color—are as follows:

Tree:
- *Density.*—Dense.
- *Size.*—Large.
- *Vigor.*—Vigorous.
- *Hardiness.*—Hardy to frost.

Trunk:
- *Form.*—Stocky.
- *Texture.*—Medium.

Branches:
- *Form.*—Stocky.
- *Texture.*—Medium.
- *Lenticels.*—Number—Numerous. Size—Large.
- *Branching habit.*—Spreading.
- *Color.*—New wood—Brown to green. Mature wood—gray.

Foliage:
- *Quantity.*—Abundant.

Leaves:
- *Size.*—Large. Average length—3¼". Average width 1".
- *Shape.*—Ovate. Acutely pointed.
- *Thickness.*—Medium.
- *Texture.*—Smooth.
- *Margin.*—Crenate.
- *Petiole.*—Medium length. Medium thickness.
- *Glands.*—Average number—6. Alternate. Medium size. Globose. Green. Positioned on petiole and base of blade.
- *Stipules.*—Wanting.
- *Color.*—Top side—Medium green (23–L–8). Under side—Lighter medium green (22–H–7).

Bloom:
- *Amount of bloom.*—Very heavy.
- *Color.*—White.
- *Blooming period.*—Average—February 12—Mar. 3. Early—about with the Nonpareil and Peerless.

Crop:
- *Bearing.*—Regular bearer.
- *Productivity.*—Very heavy.
- *Distribution of nuts on tree.*—Well distributed.
- *Ripening period.*—Average—September 1. Early—about with Nonpareil, Peerless, and Ne Plus Ultra.
- *Tenacity.*—Hangs well on tree. Easy to harvest. Easy to hull.

Hull:
- *Outer surface.*—Smooth.
- *Form.*—Irregular.
- *Thickness.*—Thick.
- *Flesh.*—Tough.
- *Suture.*—Flat depressed.
- *Color.*—Light green (20–E–5) with silvery sheen.
- *Dehiscence.*—Opens freely.
- *Splitting.*—Along suture.

Nut:
- *Size.*—Medium. Average length—1⅜". Average width—15/16". Average thickness—11/16". Average weight—4.8 grs.
- *Form.*—Length/width—Oval. Width/thickness—Medium.
- *Shell.*—Soft. Thin. Ragged. Outer shell—Crumbling. Largely missing. No adherence to hull. Inner shell—Soft. Well sealed.

*Color.*—Medium light tan (11–I–6).
*Pits.*—Small. Numerous. Shallow. Round.
*Base.*—Dorsally oblique.
*Stem scar.*—Small.
*Apex.*—Acute. Acuminate. Shouldered. Prolonged at tip.
*Wing.*—Broad. Thin. Tapered toward base.
*Inner surface.*—Medium.
*Ventral streak.*—Light. Narrow. Short. Point acute. Not corky.
*Percent of kernel to nut.*—56%–62%.

Kernel:

*Size.*—Medium. Average length—1". Average width—⅝". Average thickness—7/16". Average weight—1.725 grs.
*Form.*—Length/width—Ovate. Width/thickness—Plump. Medium.
*Base.*—Ventrally oblique.
*Stem scar*—Small. Obtuse.
*Apex.*—Acute. Acuminate. Shouldered. Tip recurved.
*Plumpness.*—Smooth. Furrowed.
*Pellicle.*—Thin.
*Pubescence.*—Smooth. Veined.
*Color.*—Medium light brown (13–L–8) with darker striations.

*Number of doubles.*—Few.
*Defective kernels.*—None observed.
*Flavor.*—Dry. Sweet.
*Quality.*—Very good.

The almond tree and its nut herein described may vary in slight detail due to climatic and soil conditions under which the variety may be grown; the present description being of the variety as grown in the Sacramento Valley of California.

I claim:

1. A new and distinct variety of almond tree, substantially as illustrated and described, particularly characterized by a tree having a branching habit generally like the Nonpareil, but with fruit wood which is thick and similar to the Drake; by a blooming period close to the Nonpareil and hence an excellent pollinator therefor; by a harvest period substantially with the Nonpareil but with a much heavier crop; and by nuts having shells and kernels of generally the same shape and color as the Davey, the nuts having a soft, well-sealed shell.

No references cited.

ROBERT E. BAGWILL, Primary Examiner